US012763173B2

(12) United States Patent
Radhakrishnan et al.

(10) Patent No.: US 12,763,173 B2
(45) Date of Patent: Oct. 13, 2026

(54) DETERMINING MOLECULES TO IMPLEMENT IN REFRIGERATION SYSTEMS

(71) Applicants: Nissan North America, Inc., Franklin, TN (US); United States of America as Represented by the Administrator of NASA, Washington, DC (US)

(72) Inventors: Balachandran Gadaguntla Radhakrishnan, Palo Alto, CA (US); Shigemasa Kuwata, Palo Alto, CA (US); Masanobu Uchimura, Palo Alto, CA (US); Yasushi Ichikawa, Hayama-machi (JP); William Curtis Tucker, San Jose, CA (US); Lauren J. Abbott, San Jose, CA (US); Ewa Papajak, Berkley, CA (US); Andrew Pablo Santos, Alameda, CA (US); Krishnan Swaminathan Gopalan, Milpitas, CA (US); Justin B. Haskins, San Jose, CA (US)

(73) Assignees: Nissan North America, Inc., Franklin, TN (US); United States of America as Represented by the Administrator of NASA, Washington, DC (US)

( * ) Notice: Subject to any disclaimer, the term of this patent is extended or adjusted under 35 U.S.C. 154(b) by 523 days.

(21) Appl. No.: 18/365,581

(22) Filed: Aug. 4, 2023

(65) Prior Publication Data

US 2025/0046400 A1 Feb. 6, 2025

(51) Int. Cl.

| | |
|---|---|
| ***G16C 20/30*** | (2019.01) |
| ***G01N 25/12*** | (2006.01) |
| ***G16C 20/70*** | (2019.01) |

(52) U.S. Cl.
CPC ............ *G16C 20/30* (2019.02); *G01N 25/12* (2013.01); *G16C 20/70* (2019.02)

(58) Field of Classification Search
CPC ......... G16C 20/30; G16C 20/70; G01N 25/12
See application file for complete search history.

(56) References Cited

U.S. PATENT DOCUMENTS

| | | | | |
|---|---|---|---|---|
| 2020/0123426 A1* | 4/2020 | Moya Raposo | ......... | C09K 5/02 |
| 2022/0051759 A1* | 2/2022 | Brereton | ................ | G16C 20/30 |
| 2024/0336821 A1* | 10/2024 | Bermúdez García | .... | C09K 5/02 |

FOREIGN PATENT DOCUMENTS

| | | | | |
|---|---|---|---|---|
| CN | 109140821 A * | 1/2019 | ............. | F25B 23/00 |

OTHER PUBLICATIONS

Garcia-Ben, et al., "Discovery of Colossal Breathing-Caloric Effect under Low Applied Pressure in the Hybrid Organic" Inorganic MIL-53(AI) Material, Chem. Mater. 2022, 34, 3323-3332. (Year: 2022).*

(Continued)

*Primary Examiner* — Catherine T. Rastovski
*Assistant Examiner* — Toni D Sauncy
(74) *Attorney, Agent, or Firm* — Young Basile Hanlon & MacFarlane, P.C.

(57) ABSTRACT

A system can train a machine learning model to predict one or more properties of a molecule. The one or more properties may include a temperature of fusion and/or an entropy of fusion. The machine learning model can be trained based on a sample of molecules from a plurality of molecules. The system can apply the machine learning model to the plurality of molecules to predict the one or more properties for molecules of the plurality of molecules. The system can determine a plurality of candidate molecules from the plurality of molecules. The plurality of candidate molecules may be determined based on the one or more properties predicted for molecules of the plurality of molecules. The (Continued)

system can determine a target molecule of the plurality of candidate molecules to implement in a refrigeration system.

18 Claims, 8 Drawing Sheets

(56) References Cited

OTHER PUBLICATIONS

Garcia-Ben, et al., "Simple and Low-Cost Footstep Energy-Recover Barocaloric Heating and Cooling Device", Materials 2021, 14, 5947. (Year: 2021).*
Alkhatib, et al., "Searching for Sustainable Refrigerants by Bridging Molecular Modeling with Machine Learning", Ind Eng Chem Res May 18, 2022;61(21):7414-7429 (Year: 2022).*
CN109140821A_FOR Reference With Translation (Year: 2019).*
Nomura, K., Nishihara, H., Yamamoto, M. et al. Force-driven reversible liquid-gas phase transition mediated by elastic nanosponges. Nat Commun 10, 2559 (2019). https://doi.org/10.1038/s41467-019-10511-7.

* cited by examiner

800

802

| IMAGE | CHEMICAL NAME | CHEMICAL FORMULA | ELEMENTS | TEMP PHASE CHANGE | ENTROPY PHASE CANGE | TEMP UNCERTAINTY | ENTROPT UNCERTAINTY | SCORE | UNCERTAINTY |
|---|---|---|---|---|---|---|---|---|---|
|  | [3-(difluoromethyl)oxetan-3-yl]methanol | C5H8F2O2 | CHFO | 303.60 | 66.10 | 65.01 | 24.86 | 5.69 | 1616.33 |
|  | 3-(difluoromethyl)azetidine-3-carbonitrile | C5H6F2N2 | CHFN | 293.20 | 64.64 | 60.96 | 27.71 | 7.99 | 1689.11 |
|  | 3-fluoro-2,2-bis(fluoromethyl)propan-1-ol | C5H9F3O | CHFO | 292.48 | 63.81 | 58.18 | 26.06 | 9.19 | 1515.99 |
|  | [3-(difluoromethyl)oxetan-3-yl]methanamine | C5H9F2NO | CHFNO | 308.10 | 62.94 | 62.80 | 21.57 | 10.44 | 1354.68 |

DETERMINING MOLECULES TO IMPLEMENT IN REFRIGERATION SYSTEMS

TECHNICAL FIELD

This application relates to refrigeration systems, such as heating, ventilation, and air conditioning (HVAC) systems, including determining molecules to implement in refrigeration systems, including refrigeration systems implemented by vehicles.

BACKGROUND

Barocaloric materials are substances that exhibit thermal change in response to pressure. In a phenomena known as the Barocaloric effect, a Barocaloric material may undergo a solid-to-solid phase transition (e.g., from one crystal structure to another), and release heat as a result of the transition, when a mechanical force or pressure is applied to the material. Some Barocaloric materials may be suitable as refrigerants in refrigeration systems, such as HVAC systems. Refrigeration systems that use Barocaloric materials may advantageously avoid leakages associated with liquids and gasses that could occur in conventional refrigeration systems.

SUMMARY

Disclosed herein are aspects, features, elements, implementations, and embodiments of determining molecules to implement in refrigeration systems, including refrigeration systems implemented by vehicles.

An aspect of the disclosed implementations is a refrigeration system including a container holding a solid refrigerant comprised of a target molecule; a structure configured to apply a pressure to the solid refrigerant; and a fan configured to conduct an airflow relative to the container. The airflow may move heated air and/or cooled air generated by applying the pressure to the solid refrigerant. The target molecule may be determined based on a machine learning model predicting one or more properties of the target molecule. The one or more properties may include a temperature of fusion ($T_{fusion}$) and/or an entropy of fusion ($\Delta S_{fusion}$). In some implementations, the target may be determined based on susceptibility to a Barocaloric effect. In some implementations, the target molecule may be a plastic crystal that is a solid at room temperature (e.g., about 300 Kelvin). In some implementations, the container, the structure, and the fan may be part of an HVAC system of a vehicle.

Another aspect of the disclosed implementations is a method including: training a machine learning model to predict one or more properties of a molecule, the one or more properties including at least one of $T_{fusion}$ or $\Delta S_{fusion}$, the machine learning model trained based on a sample of molecules; applying the machine learning model to a plurality of molecules to predict the one or more properties for molecules of the plurality of molecules; determining a plurality of candidate molecules from the plurality of molecules, the plurality of candidate molecules determined based on the one or more properties predicted for molecules of the plurality of molecules; and determining a target molecule of the plurality of candidate molecules to implement in a refrigeration system. In some implementations, the method may include determining the plurality of molecules, from a database of molecules, based on exceeding a predefined molecular weight. In some implementations, the method may include determining the plurality of molecules, from a database of molecules, based on predefined elements. In some implementations, the method may include determining the sample of molecules from the plurality of molecules. In some implementations, the one or more properties may include a solid-to-solid phase transition temperature ($T_T$). In some implementations, the one or more properties may include an entropy change during a solid-to-solid phase transition ($\Delta S_T$). In some implementations, determining the plurality of candidate molecules may include determining molecules having $T_{fusion}$ greater than a first threshold and $\Delta S_{fusion}$ less than a second threshold. In some implementations, determining the plurality of candidate molecules may include determining plastic crystals that are solids at room temperature. In some implementations, determining the target molecule may include ranking candidate molecules of the plurality of candidate molecules based on the one or more properties of the candidate molecules. In some implementations, determining the target molecule may include comparing $T_T$ of candidate molecules of the plurality of candidate molecules to an ideal $T_T$; and comparing $\Delta S_T$ of candidate molecules of the plurality of candidate molecules to an ideal $\Delta S_T$. In some implementations, the method may include physically testing the target molecule to determine one or more actual properties for the target molecule and updating the machine learning model based on results from the testing. In some implementations, implementing the target molecule may include compressing a substance, comprising the target molecule, in a container, and conducting an airflow relative to the container.

Another aspect of the disclosed implementations is a non-transitory computer readable medium storing instructions operable to cause one or more processors to perform operations comprising: determining a plurality of molecules from a database; determining a sample of molecules from the plurality of molecules; training a machine learning model to predict one or more properties of a molecule, the one or more properties indicating susceptibility to a Barocaloric effect, the machine learning model trained based on the sample of molecules; applying the machine learning model to the plurality of molecules to predict the one or more properties for molecules of the plurality of molecules; determining a plurality of candidate molecules from the plurality of molecules, the plurality of candidate molecules determined based on the one or more properties predicted for molecules of the plurality of molecules; and determining a target molecule of the plurality of candidate molecules to implement in a refrigeration system. In some implementations, the database includes at least $10^9$ molecules, the plurality of molecules includes at least $10^6$ molecules, and the plurality of candidate molecules includes at least $10^3$ molecules, and determining the plurality of molecules comprises determining molecules having elements restricted to one or more of Carbon, Hydrogen, Oxygen, Nitrogen, Bromine, Chlorine, Fluorine, and Sulfur. In some implementations, determining the plurality of candidate molecules comprises determining molecules of the plurality of molecules having $T_{fusion}$ between 350K and 450K and $\Delta S_{fusion}$ less than a 30 J/(mol-K). In some implementations, the operations further include ranking candidate molecules of the plurality of candidate molecules based on Euclidean distances between the one or more properties of the candidate molecules and one or more ideal values.

Variations in these and other aspects, features, elements, implementations, and embodiments of the methods, apparatus, procedures, and algorithms disclosed herein are described in further detail hereafter.

BRIEF DESCRIPTION OF THE DRAWINGS

The various aspects of the methods and apparatuses disclosed herein will become more apparent by referring to the examples provided in the following description and drawings in which like reference numbers refer to like elements unless otherwise noted.

DETAILED DESCRIPTION

Figure 1:
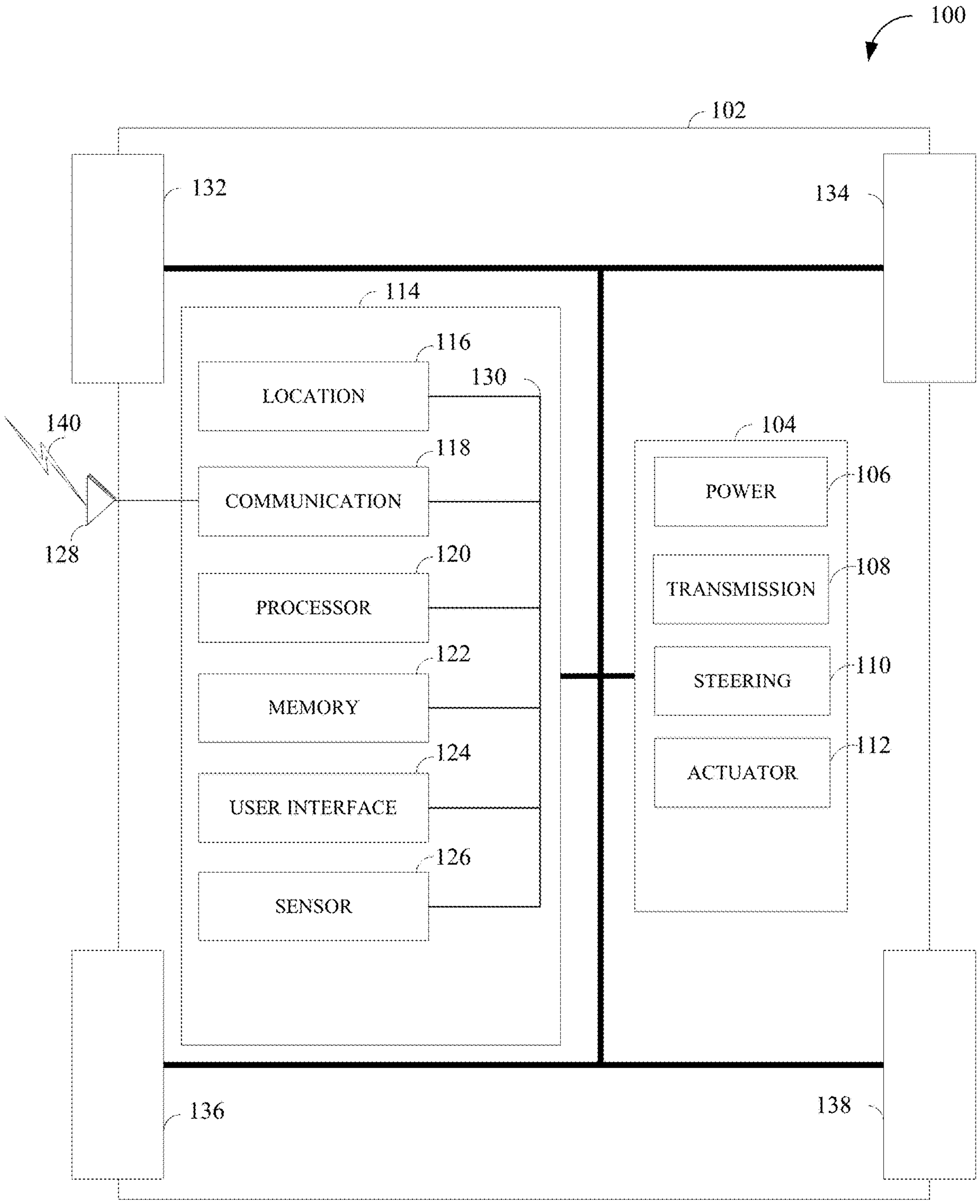
FIG. 1 is a diagram of an example of a portion of a vehicle in which the aspects, features, and elements disclosed herein may be implemented.

Barocaloric materials may be used as refrigerants in refrigeration systems, including refrigeration systems implemented by vehicles. Implementing the material as a solid, so that the material may undergo a solid-to-solid phase transition and release heat when pressure is applied, can enable a vehicle to avoid leakages associated with liquids and gasses. However, selection of a Barocaloric material for a refrigeration system can be difficult. While some plastic crystals have been identified as candidate Barocaloric materials for refrigeration systems, they are sometimes less than ideal, involving an application of relatively higher pressure, and a relatively larger mechanical system to apply the high pressure, to obtain at least a modest temperature change. Further, many Barocaloric materials, including plastic crystals, can vary significantly in terms of availability and price. As a result, even when a Barocaloric material is suitable for application in a refrigeration system, the material might not be available in sufficient quantities, and/or might be prohibitively expensive at a given time. Thus, there is a need for determining Barocaloric materials to implement in refrigeration systems, including refrigeration systems implemented by vehicles.

Implementations of this disclosure address problems such as these by utilizing a machine learning model to predict predetermined characteristics identified by the inventors (e.g., $T_{fusion}$ and/or $\Delta S_{fusion}$ in particular ranges) associated with a large set of available molecules in a database. This may enable identifying candidate molecules exhibiting improved characteristics of the Barocaloric effect (e.g., an application of relatively lower pressure to obtain a relatively higher temperature change) so that such molecules can be obtained for application in refrigeration systems on an ongoing basis.

In some implementations, a system can determine a plurality of molecules from a database. For example, the database may include many molecules, such as $10^9$ molecules or more (e.g., the Zinc20 database). The system can determine a sample of molecules from the plurality of molecules. For example, the sample of molecules may include a relatively smaller number from the plurality of molecules, such as at least 100 molecules. The system may train a machine learning model to predict one or more properties of a molecule based on the sample of molecules. The one or more properties may indicate susceptibility to the Barocaloric effect under desirable conditions. For example, the one or more properties may include a temperature of fusion ($T_{fusion}$), an entropy of fusion ($\Delta S_{fusion}$), a solid-to-solid phase transition temperature ($T_T$), and/or an entropy change during a solid-to-solid phase transition ($\Delta S_T$). The system may apply the machine learning model to the plurality of molecules from the database to predict the one or more properties for molecules of the plurality of molecules. The system may then determine a plurality of candidate molecules from the plurality of molecules. The plurality of candidate molecules may be determined based on the one or more properties predicted for molecules of the plurality of molecules (e.g., $T_{fusion}$, $\Delta S_{fusion}$, $T_T$, and/or $\Delta S_T$). The system may then determine a target molecule from the plurality of candidate molecules to implement in a refrigeration system. As a result, a molecule may be selected based on generating a larger amount of heat with the application of a lesser amount of pressure, while comprising a solid at room temperature.

In some implementations, the refrigeration system may include a container holding a solid refrigerant comprised of the target molecule. The refrigeration system may also include a structure configured to apply a pressure to the solid refrigerant. The refrigeration system may also include a fan configured to conduct an airflow relative to the container. The airflow may move heated air and/or cooled air generated by applying the pressure to the solid refrigerant. The container, the structure, and the fan may be part of an HVAC system of a vehicle.

In some implementations, a device may be configured to use pressure as a tunable parameter to cause a refrigeration effect. For example, pressure may be applied on plastic crystals to cause a solid-to-solid phase transformation (e.g., the plastic crystals may transition from an ordered structure to a disordered structure, resulting in a heating effect). The plastic crystals utilized in the device may be identified by using a machine learning model to predict $T_{fusion}$, $\Delta S_{fusion}$, $T_T$, and/or $\Delta S_T$. The plastic crystal may be restricted to those that contain Carbon (C), Hydrogen (H), Oxygen (O), Nitrogen (N), Fluorine (F), Chlorine (CI), Bromine (Br), and/or Sulfur(S). A melting/fusion temperature criteria of 350 Kelvin<$T_{fusion}$<450 Kelvin and/or an entropy change during fusion criteria of $\Delta S_{fusion}$<30 J/(mol-K) may be used. Further, to enable the material to be used in room temperature conditions while having a relatively larger refrigeration effect, a material may be selected that best satisfies a formula, such as $100*\text{sqrt}\,[((300-T_T)^2/(300)^2)-((70-\Delta S_T)^2/(70)^2)]<75$. The measure may represent a Euclidean distance from properties of an ideal candidate (e.g., $T_T$=300 Kelvin, and $\Delta S_T$=70 J/(mol-K)).

To describe some implementations in greater detail, reference is first made to examples of hardware and software structures used for determining molecules to implement in refrigeration systems, including refrigeration systems implemented by vehicles.

FIG. 1 is a diagram of an example of a portion of a vehicle 100 in which the aspects, features, and elements disclosed herein may be implemented. The vehicle 100 includes a chassis 102, a powertrain 104, a controller 114, wheels 132/134/136/138, and may include any other element or combination of elements of a vehicle. Although the vehicle 100 is shown as including four wheels 132/134/136/138 for simplicity, any other propulsion device or devices, such as a propeller or tread, may be used. In FIG. 1, the lines interconnecting elements, such as the powertrain 104, the controller 114, and the wheels 132/134/136/138, indicate that information, such as data or control signals; power, such as electrical power or torque; or both information and power may be communicated between the respective elements. For example, the controller 114 may receive power from the powertrain 104 and communicate with the powertrain 104, the wheels 132/134/136/138, or both, to control the vehicle 100, which can include accelerating, decelerating, steering, or otherwise controlling the vehicle 100.

The powertrain 104 includes a power source 106, a transmission 108, a steering unit 110, a vehicle actuator 112, and may include any other element or combination of elements of a powertrain, such as a suspension, a drive shaft, axles, or an exhaust system. Although shown separately, the wheels 132/134/136/138 may be included in the powertrain 104.

The power source 106 may be any device or combination of devices operative to provide energy, such as electrical energy, thermal energy, or kinetic energy. For example, the power source 106 includes an engine, such as an internal combustion engine, an electric motor, or a combination of an internal combustion engine and an electric motor, and is operative to provide kinetic energy as a motive force to one or more of the wheels 132/134/136/138. In some embodiments, the power source 106 includes a potential energy unit, such as one or more dry cell batteries, such as nickel-cadmium (NiCd), nickel-zinc (NiZn), nickel metal hydride (NiMH), lithium-ion (Li-ion); solar cells; fuel cells; or any other device capable of providing energy.

The transmission 108 receives energy, such as kinetic energy, from the power source 106 and transmits the energy to the wheels 132/134/136/138 to provide a motive force. The transmission 108 may be controlled by the controller 114, the vehicle actuator 112, or both. The steering unit 110 may be controlled by the controller 114, the vehicle actuator 112, or both and controls the wheels 132/134/136/138 to steer the vehicle. The vehicle actuator 112 may receive signals from the controller 114 and may actuate or control the power source 106, the transmission 108, the steering unit 110, or any combination thereof to operate the vehicle 100.

In the illustrated embodiment, the controller 114 includes a location unit 116, an electronic communication unit 118, a processor 120, a memory 122, a user interface 124, a sensor 126, and an electronic communication interface 128. Although shown as a single unit, any one or more elements of the controller 114 may be integrated into any number of separate physical units. For example, the user interface 124 and the processor 120 may be integrated in a first physical unit, and the memory 122 may be integrated in a second physical unit. Although not shown in FIG. 1, the controller 114 may include a power source, such as a battery. Although shown as separate elements, the location unit 116, the electronic communication unit 118, the processor 120, the memory 122, the user interface 124, the sensor 126, the electronic communication interface 128, or any combination thereof can be integrated in one or more electronic units, circuits, or chips.

In some embodiments, the processor 120 includes any device or combination of devices, now existing or hereafter developed, capable of manipulating or processing a signal or other information, for example optical processors, quantum processors, molecular processors, or a combination thereof. For example, the processor 120 may include one or more special-purpose processors, one or more digital signal processors, one or more microprocessors, one or more controllers, one or more microcontrollers, one or more integrated circuits, one or more Application Specific Integrated Circuits, one or more Field Programmable Gate Arrays, one or more programmable logic arrays, one or more programmable logic controllers, one or more state machines, or any combination thereof. The processor 120 may be operatively coupled with the location unit 116, the memory 122, the electronic communication interface 128, the electronic communication unit 118, the user interface 124, the sensor 126, the powertrain 104, or any combination thereof. For example, the processor may be operatively coupled with the memory 122 via a communication bus 130.

The processor 120 may be configured to execute instructions. Such instructions may include instructions for remote operation, which may be used to operate the vehicle 100 from a remote location, including the operations center. The instructions for remote operation may be stored in the vehicle 100 or received from an external source, such as a traffic management center, or server computing devices, which may include cloud-based server computing devices.

The memory 122 may include any tangible non-transitory computer-usable or computer readable medium capable of, for example, containing, storing, communicating, or transporting machine-readable instructions or any information associated therewith, for use by or in connection with the processor 120. The memory 122 may include, for example, one or more solid state drives, one or more memory cards, one or more removable media, one or more read-only memories (ROM), one or more random-access memories (RAM), one or more registers, one or more low power double data rate (LPDDR) memories, one or more cache memories, one or more disks (including a hard disk, a floppy disk, or an optical disk), a magnetic or optical card, or any type of non-transitory media suitable for storing electronic information, or any combination thereof.

The electronic communication interface 128 may be a wireless antenna, as shown, a wired communication port, an optical communication port, or any other wired or wireless unit capable of interfacing with a wired or wireless electronic communication medium 140.

The electronic communication unit 118 may be configured to transmit or receive signals via the wired or wireless electronic communication medium 140, such as via the electronic communication interface 128. Although not explicitly shown in FIG. 1, the electronic communication unit 118 is configured to transmit, receive, or both via any wired or wireless communication medium, such as radio frequency (RF), ultraviolet (UV), visible light, fiber optic, wire line, or a combination thereof. Although FIG. 1 shows a single one of the electronic communication unit 118 and a single one of the electronic communication interface 128, any number of communication units and any number of communication interfaces may be used. In some embodiments, the electronic communication unit 118 can include a dedicated short-range communications (DSRC) unit, a wireless safety unit (WSU), IEEE 802.11p (WiFi-P), or a combination thereof.

The location unit 116 may determine geolocation information, including but not limited to longitude, latitude, elevation, direction of travel, or speed, of the vehicle 100. For example, the location unit includes a global positioning system (GPS) unit, such as a Wide Area Augmentation System (WAAS) enabled National Marine Electronics Association (NMEA) unit, a radio triangulation unit, or a combination thereof. The location unit 116 can be used to obtain information that represents, for example, a current heading of the vehicle 100, a current position of the vehicle 100 in two or three dimensions, a current angular orientation of the vehicle 100, or a combination thereof.

The user interface 124 may include any unit capable of being used as an interface by a person, including any of a virtual keypad, a physical keypad, a touchpad, a display, a touchscreen, a speaker, a microphone, a video camera, a sensor, and a printer. The user interface 124 may be operatively coupled with the processor 120, as shown, or with any other element of the controller 114. Although shown as a single unit, the user interface 124 can include one or more physical units. For example, the user interface 124 includes an audio interface for performing audio communication with a person, and a touch display for performing visual and touch-based communication with the person.

The sensor 126 may include one or more sensors, such as an array of sensors, which may be operable to provide information that may be used to control the vehicle. The sensor 126 can provide information regarding current operating characteristics of the vehicle or its surroundings (e.g., movement information associated with an object traveling in front of the vehicle, and road information associated with a vehicle transportation network). The sensor 126 includes, for example, a speed sensor, acceleration sensors, a steering angle sensor, traction-related sensors, braking-related sensors, or any sensor, or combination of sensors, which is operable to report information regarding some aspect of the current dynamic situation of the vehicle 100.

In some embodiments, the sensor 126 includes sensors that are operable to obtain information regarding the physical environment surrounding the vehicle 100. For example, one or more sensors detect road geometry and obstacles, such as fixed obstacles, vehicles, cyclists, and pedestrians. The sensor 126 can be or include one or more video cameras, laser-sensing systems, infrared-sensing systems, acoustic-sensing systems, or any other suitable type of on-vehicle environmental sensing device, or combination of devices, now known or later developed. The sensor 126 and the location unit 116 may be combined.

Although not shown separately, the vehicle 100 may include a trajectory controller. For example, the controller 114 may include a trajectory controller. The trajectory controller may be operable to obtain information describing a current state of the vehicle 100 and a route planned for the vehicle 100, and, based on this information, to determine and optimize a trajectory for the vehicle 100. In some embodiments, the trajectory controller outputs signals operable to control the vehicle 100 such that the vehicle 100 follows the trajectory that is determined by the trajectory controller. For example, the output of the trajectory controller can be an optimized trajectory that may be supplied to the powertrain 104, the wheels 132/134/136/138, or both. The optimized trajectory can be a control input, such as a set of steering angles, with each steering angle corresponding to a point in time or a position. The optimized trajectory can be one or more paths, lines, curves, or a combination thereof.

One or more of the wheels 132/134/136/138 may be a steered wheel, which is pivoted to a steering angle under control of the steering unit 110; a propelled wheel, which is torqued to propel the vehicle 100 under control of the transmission 108; or a steered and propelled wheel that steers and propels the vehicle 100.

A vehicle may include units or elements not shown in FIG. 1, such as an enclosure, a Bluetooth® module, a frequency modulated (FM) radio unit, a Near-Field Communication (NFC) module, a liquid crystal display (LCD) display unit, an organic light-emitting diode (OLED) display unit, a speaker, or any combination thereof.

The vehicle, such as the vehicle 100, may be an autonomous vehicle or a semi-autonomous vehicle. For example, as used herein, an autonomous vehicle as used herein should be understood to encompass a vehicle that includes an advanced driver assist system (ADAS). An ADAS can automate, adapt, and/or enhance vehicle systems for safety and better driving such as by circumventing or otherwise correcting driver errors.

Figure 2:
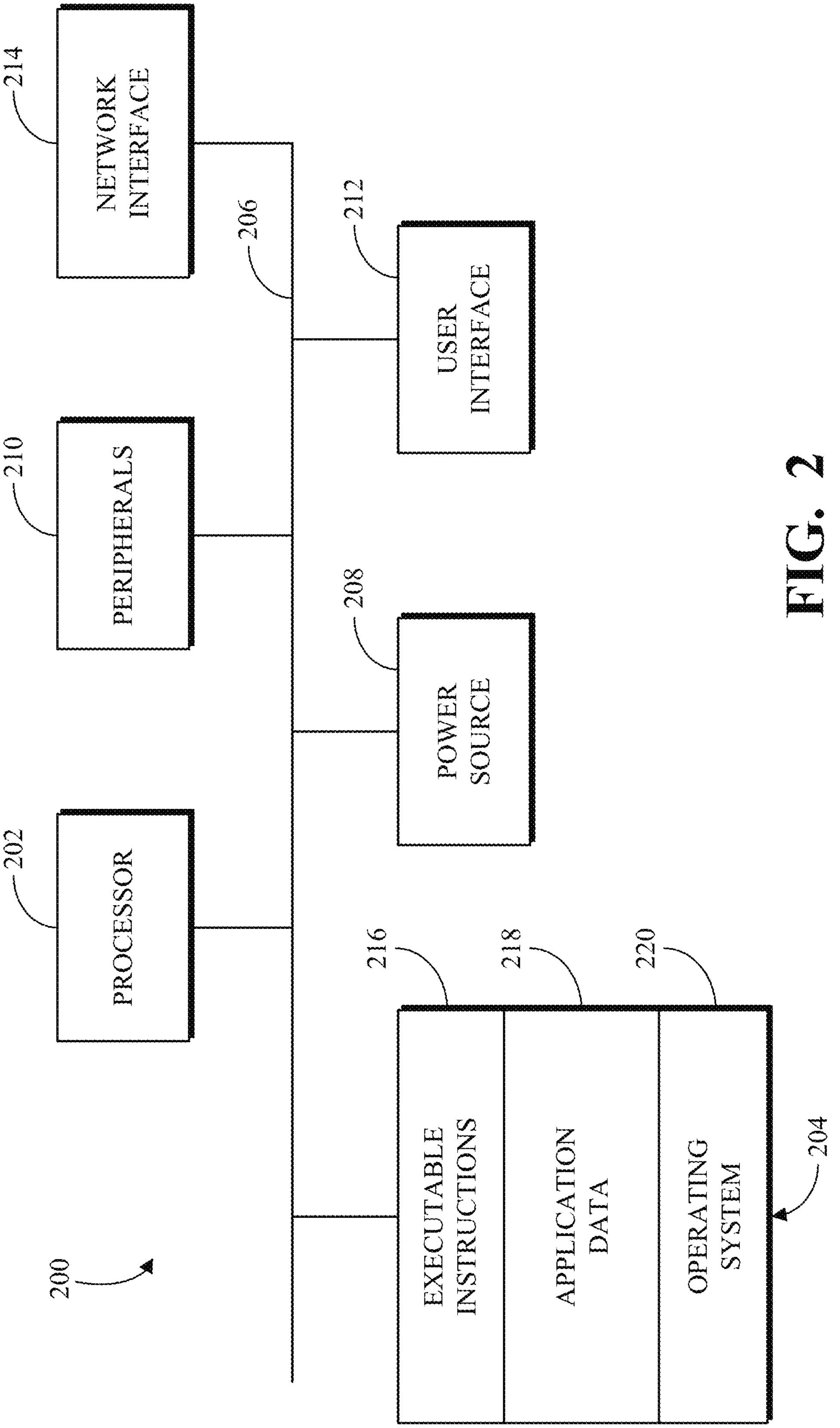
FIG. 2 is a block diagram of an example internal configuration of a computing device of an electronic computing and communications system.

FIG. 2 is a block diagram of an example internal configuration of a computing device 200 of an electronic computing and communications system. In one configuration, the computing device 200 may determine molecules to implement in refrigeration systems, including a refrigeration system implemented by the vehicle 100 shown in FIG. 1.

The computing device 200 includes components or units, such as a processor 202, a memory 204, a bus 206, a power source 208, peripherals 210, a user interface 212, a network interface 214, other suitable components, or a combination thereof. One or more of the memory 204, the power source 208, the peripherals 210, the user interface 212, or the network interface 214 can communicate with the processor 202 via the bus 206.

The processor 202 is a central processing unit, such as a microprocessor, and can include single or multiple processors having single or multiple processing cores. Alternatively, the processor 202 can include another type of device, or multiple devices, configured for manipulating or processing information. For example, the processor 202 can include multiple processors interconnected in one or more manners, including hardwired or networked. The operations of the processor 202 can be distributed across multiple devices or units that can be coupled directly or across a local area or other suitable type of network. The processor 202 can include a cache, or cache memory, for local storage of operating data or instructions.

The memory 204 includes one or more memory components, which may each be volatile memory or non-volatile memory. For example, the volatile memory can be random access memory (RAM) (e.g., a DRAM module, such as DDR DRAM). In another example, the non-volatile memory of the memory 204 can be a disk drive, a solid state drive, flash memory, or phase-change memory. In some implementations, the memory 204 can be distributed across multiple devices. For example, the memory 204 can include network-based memory or memory in multiple clients or servers performing the operations of those multiple devices.

The memory 204 can include data for immediate access by the processor 202. For example, the memory 204 can include executable instructions 216, application data 218, and an operating system 220. The executable instructions 216 can include one or more application programs, which can be loaded or copied, in whole or in part, from non-volatile memory to volatile memory to be executed by the processor 202. For example, the executable instructions 216 can include instructions for performing some or all of the techniques of this disclosure. The application data 218 can include user data, database data (e.g., database catalogs or dictionaries), or the like. In some implementations, the application data 218 can include functional programs, such as a web browser, a web server, a database server, another program, or a combination thereof. The operating system 220 can be, for example, Microsoft Windows®, Mac OS X®, or Linux®; an operating system for a mobile device, such as a smartphone or tablet device; or an operating system for a non-mobile device, such as a mainframe computer.

The power source 208 provides power to the computing device 200. For example, the power source 208 can be an interface to an external power distribution system. In another example, the power source 208 can be a battery, such as where the computing device 200 is a mobile device or is otherwise configured to operate independently of an external power distribution system. In some implementations, the computing device 200 may include or otherwise use multiple power sources. In some such implementations, the power source 208 can be a backup battery.

The peripherals 210 includes one or more sensors, detectors, or other devices configured for monitoring the computing device 200 or the environment around the computing device 200. For example, the peripherals 210 can include a geolocation component, such as a global positioning system location unit. In another example, the peripherals can include a temperature sensor for measuring temperatures of components of the computing device 200, such as the processor 202. In some implementations, the computing device 200 can omit the peripherals 210.

The user interface 212 includes one or more input interfaces and/or output interfaces. An input interface may, for example, be a positional input device, such as a mouse, touchpad, touchscreen, or the like; a keyboard; or another suitable human or machine interface device. An output interface may, for example, be a display, such as a liquid crystal display, a cathode-ray tube, a light emitting diode display, virtual reality display, or other suitable display.

The network interface 214 provides a connection or link to a network. The network interface 214 can be a wired network interface or a wireless network interface. The computing device 200 can communicate with other devices via the network interface 214 using one or more network protocols, such as using Ethernet, transmission control protocol (TCP), internet protocol (IP), power line communication, an IEEE 802.X protocol (e.g., Wi-Fi, Bluetooth, or ZigBee), infrared, visible light, general packet radio service (GPRS), global system for mobile communications (GSM), code-division multiple access (CDMA), Z-Wave, another protocol, or a combination thereof.

Figure 3:
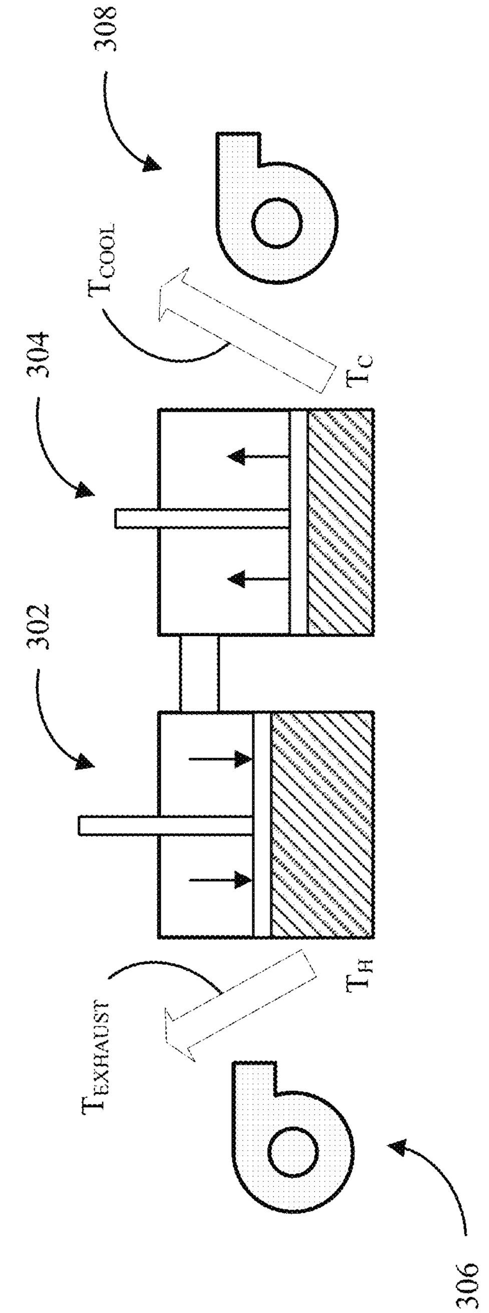
FIG. 3 is a diagram of an example of a refrigeration system that is part of an HVAC system implemented by a vehicle.

FIG. 3 is a diagram of an example of a refrigeration system 300 that may be part of a ventilation or an HVAC system implemented by the vehicle 100 shown in FIG. 1. The refrigeration system 300 may include a first container 302, a second container 304, a first fan 306, and a second fan 308. In some implementations, the refrigeration system 300 can include fewer components, such as one container and one fan (e.g., the first container 302 and the first fan 306), as opposed to two containers and two fans as shown. The first container 302 can hold a first solid refrigerant (i.e., substance) comprised of a target molecule (e.g., a Barocaloric material, such as a plastic crystal that is a solid at room temperature). A first mechanical structure may be configured to apply a pressure (e.g., a mechanical force to compress) to the first solid refrigerant in the first container 302 (e.g., in response to the controller 114). When the pressure is applied, the first solid refrigerant may undergo a solid-to-solid phase transition and release heat ($T_H$). The first fan 306 may conduct a first airflow ($T_{EXHAUST}$) relative to the first container 302. The first airflow can move the heated air generated by applying the pressure to the first solid refrigerant. For example, the first airflow may exhaust the heated air from the vehicle 100.

The second container 304 can hold a second solid refrigerant comprised of the target molecule. In some implementations, the second solid refrigerant may be comprised of a second target molecule (e.g., another Barocaloric material, such as a another a plastic crystal that is a solid at room temperature). A second mechanical structure may be configured to release pressure from the second solid refrigerant in the second container 304 (e.g., in response to the controller 114). When the pressure is released, the second solid refrigerant may undergo a solid-to-solid phase transition and absorb heat ($T_L$). The second fan 308 may conduct a second airflow ($T_{COOL}$) relative to the second container 304. The second airflow can move cooled air generated by releasing the pressure from the second solid refrigerant. For example, the second airflow may vent the cooled air into the vehicle 100.

The refrigeration system 300 can further operate in the opposite manner from that shown. For example, the first mechanical structure can release pressure from the first solid refrigerant in the first container 302 to exhaust cooled air from the vehicle 100, and the second mechanical structure can apply pressure to the second solid refrigerant in the second container 304 to vent heated air into the vehicle 100. As a result, the refrigeration system 300 can be configured to use pressure as a tunable parameter to cause a refrigeration effect in the vehicle 100.

The target molecule used in the refrigeration system 300 may be determined based on a machine learning model predicting one or more properties indicating susceptibility to the Barocaloric effect. For example, the machine learning model may predict one or more properties indicating $T_{fusion}$, $\Delta S_{fusion}$, $T_T$, and/or $\Delta S_T$. This may enable the target molecule to be determined based on susceptibility to the Barocaloric effect. As a result, an optimum Barocaloric material which may undergo a phase transition due to pressure, along with a large entropy change, may be selected for application in the refrigeration system 300.

Figure 4:
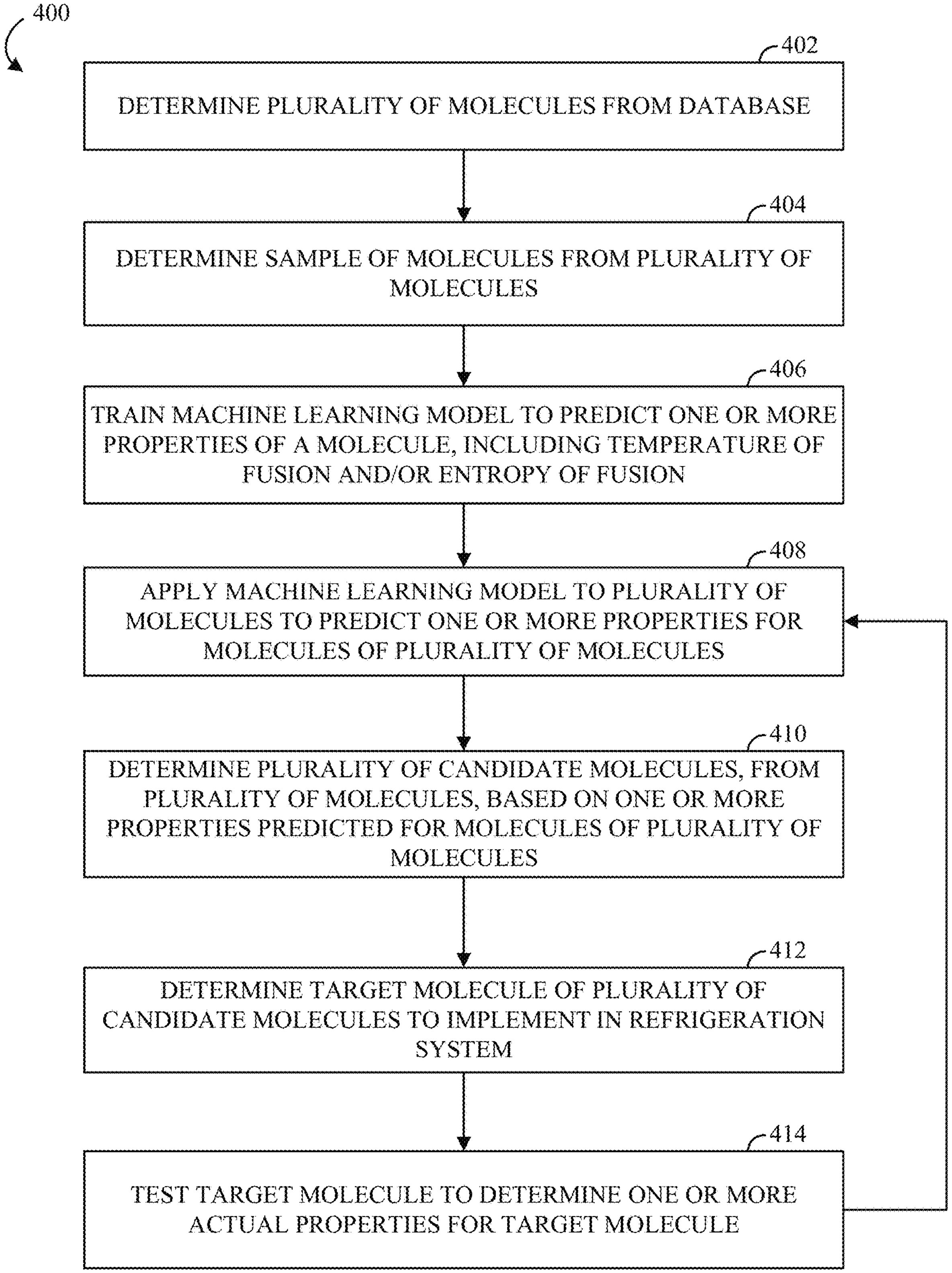
FIG. 4 is a flowchart of an example of a method for determining molecules to implement in refrigeration systems.

FIG. 4 is a flowchart of an example of a method 400 for determining molecules to implement in refrigeration systems. The method 400 can be executed using computing devices, such as the systems, hardware, and software described with respect to FIGS. 1-3. For example, the method 400 can be executed to determine the target molecule for the refrigeration system 300. In some implementations, the method 400 can be executed to determine multiple target molecules for the refrigeration system 300, such as a first target molecule utilized for the first solid state refrigerant in the first container 302, and a second target molecule utilized for the second solid state refrigerant in the second container 304. The method 400 can be performed, for example, by executing a machine-readable program or other computer-executable instructions, such as routines, instructions, programs, or other code. The steps, or operations, of the method 400 or another technique, method, process, or algorithm described in connection with the implementations disclosed herein can be implemented directly in hardware, firmware, software executed by hardware, circuitry, or a combination thereof.

For simplicity of explanation, the method 400 is depicted and described herein as a series of steps or operations. However, the steps or operations in accordance with this disclosure can occur in various orders and/or concurrently. Additionally, other steps or operations not presented and described herein may be used. Furthermore, not all illustrated steps or operations may be required to implement a technique in accordance with the disclosed subject matter.

At 402, the system may determine a plurality of molecules from a database. For example, the database may include many molecules, such as $10^9$ molecules or more. The database could be an open source database that includes some material properties associated with existing compounds, such as the Zinc20 database. The database may change over time as molecules are added and/or subtracted. The molecules in the database may vary in terms of suitability for application as refrigerants (e.g., in the refrigeration system 300), availability (e.g., stock available for purchase), and price.

The molecules in the database may be initially screened to determine the plurality of molecules. For example, the $10^9$ molecules in the database may be screened to determine $10^6$ molecules or more (e.g., 4 million molecules). Screening the molecules in the database may enable eliminating many molecules early based on preestablished criteria. This may provide a speed and/or efficiency advantage in the determination process. In some implementations, the plurality of molecules may be determined from the database based on molecules having predefined elements. For example, the plurality of molecules may be restricted to molecules having particular elements, such as one or more of Carbon, Hydrogen, Oxygen, Nitrogen, Bromine, Chlorine, Fluorine, and Sulfur. In some implementations, the plurality of molecules may be restricted to Halides. In some implementations, the plurality of molecules may be determined from the database (e.g., screened) based on molecules exceeding a predefined molecular weight, such as selecting molecules that are less than 250 Daltons. In some implementations, the plurality of molecules may be determined from the database based on molecules being currently available for purchase. In some implementations, the plurality of molecules may be determined from the database based on molecules being below a predefined price threshold.

At 404, the system may determine a sample of molecules from the plurality of molecules (e.g., a training dataset). For example, the sample of molecules could be 100 molecules or more (e.g., 174 molecules), selected from the $10^9$ molecules or more that have been screened from the database. In some implementations, the sample of molecules may be randomly selected from the plurality of molecules.

As disclosed herein, the present inventors have recognized that $T_{fusion}$ and/or $\Delta S_{fusion}$ can be used to identify plastic crystals to use in a refrigeration system, and that a machine learning model may be configured to predict the $T_{fusion}$ and/or $\Delta S_{fusion}$. At 406, the system may train a machine learning model to predict one or more properties of a molecule that indicate susceptibility to the Barocaloric effect. In some implementations, the one or more properties may include $T_{fusion}$ and/or $\Delta S_{fusion}$. In some implementations, the one or more properties may also include $T_T$ and/or $\Delta S_T$. The machine learning model may be trained based on the sample of molecules (e.g., the training dataset). In some implementations, the machine learning may be trained to identify plastic crystals that have demonstrated Barocaloric effects, such as neo-pentyl glycol (NPG). For example, the machine learning may be trained to identify plastic crystals that undergo a solid to solid phase transition accompanied by an entropy change where a refrigeration effect can be achieved by tuning the entropy change (e.g., in the refrigeration system 300).

To make the predictions, the machine learning model may be trained using $T_{fusion}$, $\Delta S_{fusion}$, $T_T$, and/or $\Delta S_T$ from the sample of molecules. For example, $T_{fusion}$, $\Delta S_{fusion}$, $T_T$, and/or $\Delta S_T$ can be used to identify plastic crystals of interest. The machine learning model can be trained using a training data set including data samples representing $T_{fusion}$, $\Delta S_{fusion}$, $T_T$, and/or $\Delta S_T$ for molecules, including plastic crystals. The training data set can enable the machine learning model to learn patterns, such as $T_{fusion}$, $\Delta S_{fusion}$, $T_T$, and/or $\Delta S_T$, to make the predictions. The training can be periodic, such as by updating the machine learning model on a discrete time interval basis (e.g., once per week or month), or otherwise. The training data set may derive from the sample of molecules. The training data set may omit certain data samples that are determined to be outliers. The machine learning model may, for example, be or include one or more of a neural network (e.g., a convolutional neural network, recurrent neural network, deep neural network, or other neural network), decision tree, vector machine, Bayesian network, cluster-based system, genetic algorithm, deep learning system separate from a neural network, or other machine learning model.

Figure 5:
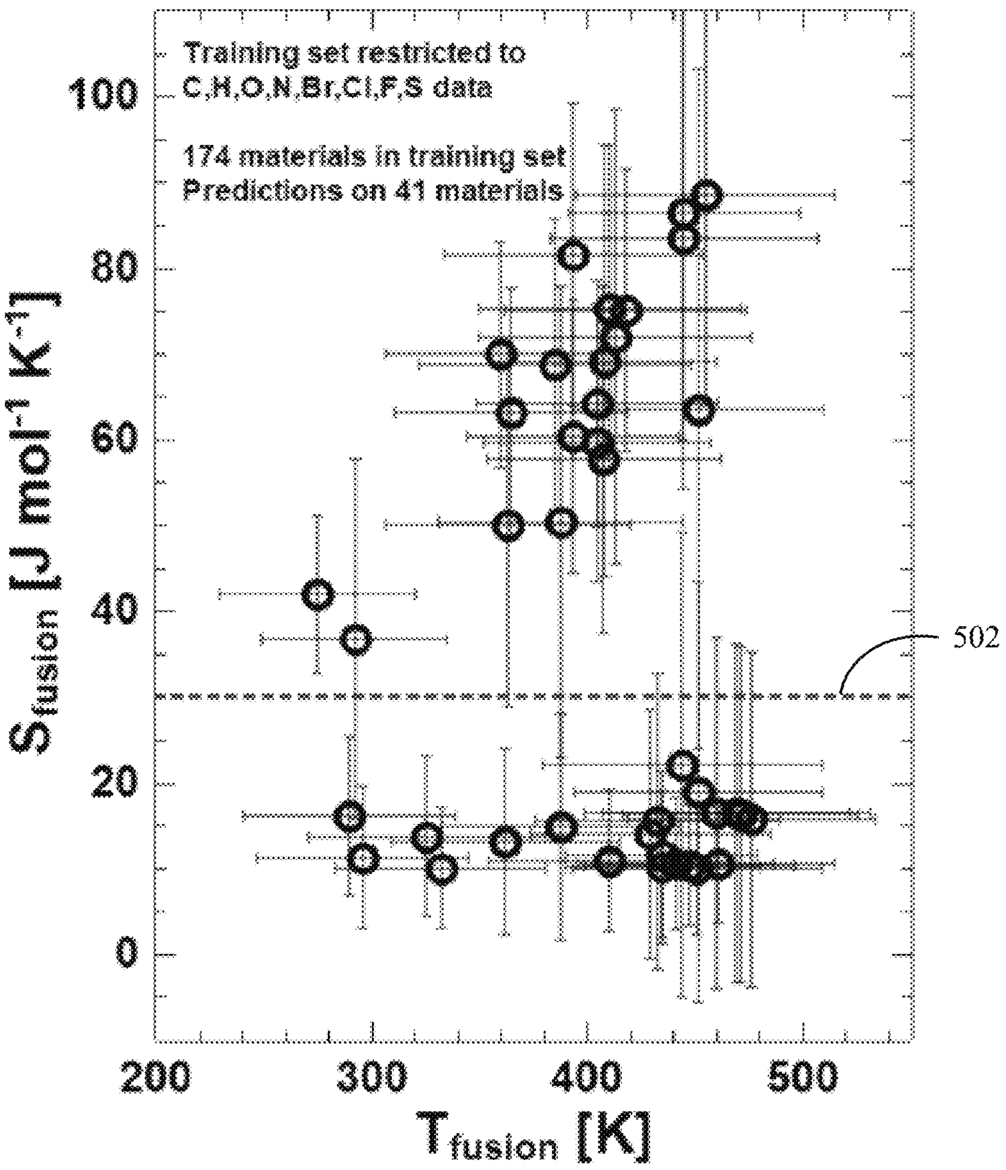
FIG. 5 is a graph of an example of training a machine learning model to predict one or more properties of a molecule based on a sample of molecules.

Training the machine learning model may include generating an initial set of predictions. For example, with additional reference to FIG. 5, the machine learning model may be trained to generate predictions for the sample of molecules (e.g., 174 molecules). The sample of molecules may be restricted to molecules including C, H, O, N, Br, Cl, F, and/or S based on the initial screening in step 402. Training the model with restrictions to predefined elements may enable an improved accuracy of the predictions. As shown in FIG. 5, the predictions from the training may include $T_{fusion}$ and $\Delta S_{fusion}$ plotted relative to one another in a graph, with standard deviations determined for each prediction (e.g., a first standard deviation for $T_{fusion}$, and a second standard deviation for $\Delta S_{fusion}$, for each prediction). The standard deviations may enable subsequent determinations of molecules with increased confidence (e.g., a lower standard deviation may be associated with a higher confidence in a molecule). A threshold 502 may represent a cutoff for an entropy change during fusion (e.g., $\Delta S_{fusion}$<30 J/(mol-K)). Molecules below the threshold 502 may be used to indicate a higher probability of plastic crystals exhibiting the Barocaloric effect.

Figure 6:
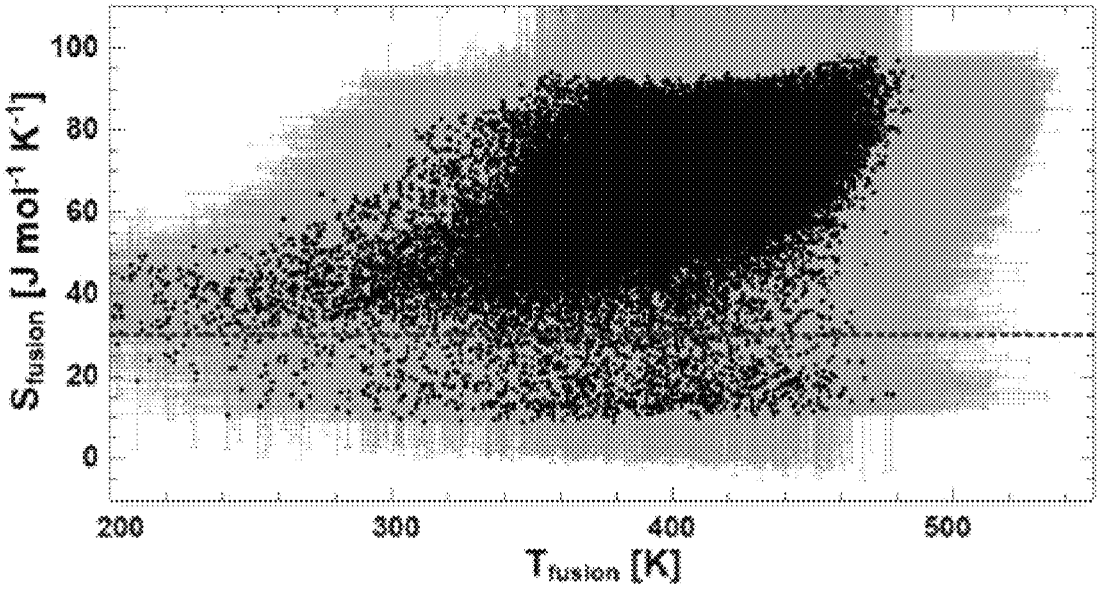
FIG. 6 is a graph of an example of applying a machine learning model to a plurality of molecules to predict one or more properties for molecules of the plurality of molecules.

At 408, the system may apply the machine learning model to the plurality of molecules (e.g., a candidate pool) selected from the database to predict the one or more properties for molecules of the plurality of molecules. This may result in a prediction dataset including $T_{fusion}$, $\Delta S_{fusion}$, $T_T$, and/or $\Delta S_T$. The system may apply the machine learning model after the training. For example, with additional reference to FIG. 6, the machine learning model may generate predictions including $T_{fusion}$ and $\Delta S_{fusion}$ for the plurality of molecules (e.g., predictions for 4 million molecules). The predictions for $T_{fusion}$ and $\Delta S_{fusion}$ are plotted relative to one another in a graph with standard deviations determined for each prediction (e.g., a first standard deviation for $T_{fusion}$, and a second standard deviation for $\Delta S_{fusion}$, for each prediction).

Figure 7:
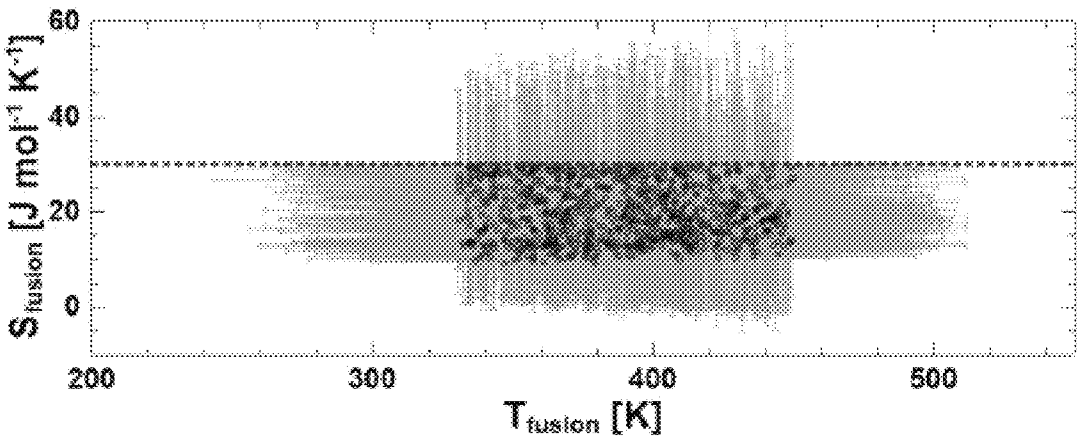
FIG. 7 is a graph of an example of determining a plurality of candidate molecules from a plurality of molecules.

At 410, the system may determine a plurality of candidate molecules from the plurality of molecules (e.g., the best candidates available, based on the predictions). The plurality of molecules may be screened to determine the plurality of candidate molecules, such as $10^6$ molecules or more screened to determine $10^3$ molecules or more. Screening the molecules may provide a speed and/or efficiency advantage. The plurality of candidate molecules may be determined based on the one or more properties predicted for the molecules (e.g., based on $T_{fusion}$, $\Delta S_{fusion}$, $T_T$, and/or $\Delta S_T$). In some implementations, determining the plurality of candidate molecules may include determining molecules of the plurality of molecules having $T_{fusion}$ greater than a first threshold and $\Delta S_{fusion}$ less than a second threshold. For example, with additional reference to FIG. 7 the plurality of candidate molecules may be selected based on having $T_{fusion}$ between 350K and 450K and $\Delta S_{fusion}$ less than a 30 J/(mol-K) (e.g., a melting/fusion temperature criteria of 350 Kelvin$<T_{fusion}<$450 Kelvin, and an entropy change during fusion criteria of $\Delta S_{fusion}<$30 J/(mol-K)). Molecules having $T_{fusion}$ between 350K and 450K may represent solids that undergo solid-to-solid phase transitions around room temperature. Molecules having $\Delta S_{fusion}<$30 J/(mol-K) may represent plastic crystal exhibiting the Barocaloric effect. This combination may advantageously narrow the field to plastic crystal that undergo solid-to-solid phase transitions around room temperature.

Figure 8:
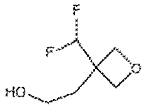
FIG. 8 is an example of ranking candidate molecules based on one or more properties to determine a target molecule.
Figure 8:
Figure 8:
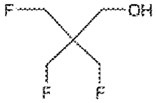
Figure 8:
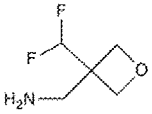

At 412, the system may determine a target molecule, of the plurality of candidate molecules, to implement in a refrigeration system (e.g., the refrigeration system 300). In some implementations, the system may rank candidate molecules based on the one or more properties (e.g., based on $T_{fusion}$, $\Delta S_{fusion}$, $T_T$, and/or $\Delta S_T$). For example, with additional reference to FIG. 8, the system may rank the plurality of candidate molecules of FIG. 7, based on a score, and output the ranking in a graphical user interface (GUI) 800. The system may generate the GUI 800 to include the plurality of candidate molecules for output to a display (e.g., the user interface 212). The GUI 800 may indicate the plurality of candidate molecules, ranked according to score. The GUI 800 may also indicate information about each candidate molecule, such as an image, chemical name, chemical formula, elements of the chemical formula (e.g., the restricted elements from the initial screening, such as C, H, O, N, F, Cl, Br, and/or S), $T_{fusion}$, $\Delta S_{fusion}$, $T_{fusion}$ uncertainty, $\Delta S_{fusion}$ uncertainty, score, and overall uncertainty.

The score may be calculated based on the one or more properties predicted. In some implementations, the score may be a Euclidean score that is determined based on Euclidean distances between the one or more properties of the candidate molecules and one or more ideal values. For example, the system could compare $T_{fusion}$ of candidate molecules to an ideal $T_{fusion}$, $\Delta S_{fusion}$ of candidate molecules to an ideal $\Delta S_{fusion}$, $T_T$ of candidate molecules to an ideal $T_T$, and $\Delta S_T$ of candidate molecules to an ideal $\Delta S_T$. Further, to enable the material to be used in room temperature conditions while having a relatively larger refrigeration effect, a material may be selected that best satisfies a formula, such as $100*\mathrm{sqrt}\,[((300-T_T)^2/(300)^2)-((70-\Delta S_T)^2/(70)^2)]<75$. The measure may represent a Euclidean distance from properties of an ideal candidate (e.g., $T_T$=300 Kelvin, about room temperature, and $\Delta S_T$=70 J/(mol-K), a relatively large entropy change). In some implementations, the target molecule that is selected may be the top ranked or best scoring candidate molecule (e.g., lowest score value), such as a target molecule 802. As a result, the target molecule may be selected so that the molecule is a plastic crystal that is a solid at room temperature and susceptible to the Barocaloric effect.

At 414, the system may test the target molecule to determine one or more actual properties for the target molecule. For example, the target molecule could be tested in the refrigeration system 300 utilized by the vehicle 100. The target molecule could be tested to determine the actual $T_{fusion}$, $\Delta S_{fusion}$, $T_T$, and/or $\Delta S_T$ of the molecule. In some implementations, the testing may comprise actual $T_{fusion}$, $\Delta S_{fusion}$, $T_T$, and/or $\Delta S_T$ of molecules from refrigeration systems implemented by a fleet of vehicles. The system may then update the machine learning model based on the testing (e.g., the actual $T_{fusion}$, $\Delta S_{fusion}$, $T_T$, and/or $\Delta S_T$ of the molecule). The system may then return to step 408 to again predict the one or more properties for molecules of the plurality of molecules (e.g., to predict $T_{fusion}$, $\Delta S_{fusion}$, $T_T$, and/or $\Delta S_T$). In some implementations, multiple candidate molecules can be tested, and the machine learning model updated, before selecting a particular target molecule to implement in a refrigeration system.

As a result, as opposed to using a known Barocaloric material with acceptable properties for use in a refrigeration system (e.g., the refrigeration system 300), aspects disclosed herein enable an improved selection of Barocaloric material by identifying plastic crystals using $T_{fusion}$ and $\Delta S_{fusion}$. Then, from a large candidate pool, a particular Barocaloric material can be determined using a machine learning model. Further, a Euclidean score may identify a best candidate molecule (e.g., the target molecule). This may enable a rapid exploration of many compounds as databases, such as Zinc20, which may continue to change on an ongoing basis.

As used herein, the terminology "processor", "computer", or "computing device" includes any unit, or combination of units, capable of performing any method, or any portion or portions thereof, disclosed herein. Also, the terminology "instructions" may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. In some implementations, instructions, or a portion thereof, may be implemented as a special-purpose processor or circuitry that may include specialized hardware for carrying out any of the methods, algorithms, aspects, or combinations thereof, as described herein. In some implementations, portions of the instructions may be distributed across multiple processors on a single device, or on multiple devices, which may communicate directly or across a network, such as a local area network, a wide area network, the Internet, or a combination thereof.

As used herein, the terminology "example," "embodiment," "implementation," "aspect," "feature," or "element" indicate serving as an example, instance, or illustration. Unless expressly indicated otherwise, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "determine" and "identify," or any variations thereof, includes selecting, ascertaining, computing, looking up, receiving, determining, establishing, obtaining, or otherwise identifying or determining in any manner whatsoever using one or more of the devices shown and described herein.

As used herein, the terminology "or" is intended to mean an inclusive "or" rather than an exclusive "or." That is, unless specified otherwise or clearly indicated otherwise by the context, "X includes A or B" is intended to indicate any of the natural inclusive permutations thereof. If X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

Further, for simplicity of explanation, although the figures and descriptions herein may include sequences or series of operations or stages, elements of the methods disclosed herein may occur in various orders or concurrently. Additionally, elements of the methods disclosed herein may occur with other elements not explicitly presented and described herein. Furthermore, not all elements of the methods described herein may be required to implement a method in accordance with this disclosure. Although aspects, features, and elements are described herein in particular combinations, each aspect, feature, or element may be used independently or in various combinations with or without other aspects, features, and/or elements.

While the disclosed technology has been described in connection with certain embodiments, it is to be understood that the disclosed technology is not to be limited to the disclosed embodiments but, on the contrary, is intended to cover various modifications and equivalent arrangements included within the scope of the appended claims, which scope is to be accorded the broadest interpretation as is permitted under the law so as to encompass all such modifications and equivalent arrangements.

What is claimed is:

1. A refrigeration system, comprising:
- a container holding a solid refrigerant comprised of a target molecule;
- a structure configured to apply a pressure to the solid refrigerant; and
- a fan configured to conduct an airflow relative to the container, the airflow moving at least one of heated air or cooled air generated by applying the pressure to the solid refrigerant,
- wherein the target molecule is determined based on a machine learning model predicting one or more properties of the target molecule, the one or more properties including at least one of a temperature of fusion ($T_{fusion}$) or an entropy of fusion ($\Delta S_{fusion}$), wherein the $T_{fusion}$ is greater than a first threshold and the $\Delta S_{fusion}$ is less than a second threshold for the target molecule.

2. The refrigeration system of claim 1, wherein the target molecule is determined based on susceptibility to a Barocaloric effect.

3. The refrigeration system of claim 1, wherein the target molecule is a plastic crystal that is a solid at room temperature.

4. The refrigeration system of claim 1, wherein the container, the structure, and the fan are part of a heating, ventilation, and air conditioning (HVAC) system of a vehicle.

5. A method, comprising:
- training a machine learning model to predict one or more properties of a molecule, the one or more properties including at least one of a temperature of fusion ($T_{fusion}$) or an entropy of fusion ($\Delta S_{fusion}$), the machine learning model trained based on a sample of molecules;
- applying the machine learning model to a plurality of molecules to predict the one or more properties for molecules of the plurality of molecules;
- determining a plurality of candidate molecules from the plurality of molecules, the plurality of candidate molecules determined based on the one or more properties predicted for molecules of the plurality of molecules; and
- determining a target molecule of the plurality of candidate molecules to implement in a refrigeration system, wherein determining the plurality of candidate molecules comprises:
- determining molecules of the plurality of molecules having $T_{fusion}$ greater than a first threshold and $\Delta S_{fusion}$ less than a second threshold.

6. The method of claim 5, further comprising:
- determining the plurality of molecules from a database of molecules, the plurality of molecules determined based on exceeding a predefined molecular weight.

7. The method of claim 5, further comprising:
- determining the plurality of molecules from a database of molecules, the plurality of molecules determined based on having predefined elements.

8. The method of claim 5, further comprising:
- determining the sample of molecules from the plurality of molecules.

9. The method of claim 5, wherein the one or more properties further include a solid-to-solid phase transition temperature ($T_T$).

10. The method of claim 5, wherein the one or more properties further include an entropy change during a solid-to-solid phase transition ($\Delta S_T$).

11. The method of claim 5, wherein determining the plurality of candidate molecules comprises:
- determining plastic crystals that are solids at room temperature.

12. The method of claim 5, wherein determining the target molecule comprises:
- ranking candidate molecules of the plurality of candidate molecules based on the one or more properties of the candidate molecules.

13. The method of claim 5, wherein determining the target molecule comprises:
- comparing $T_T$ of candidate molecules of the plurality of candidate molecules to an ideal $T_T$; and
- comparing $\Delta S_T$ of candidate molecules of the plurality of candidate molecules to an ideal $\Delta S_T$.

14. The method of claim 5, further comprising:
- testing the target molecule to determine one or more actual properties for the target molecule; and
- updating the machine learning model based on the testing.

15. The method of claim 5, wherein implementing the target molecule in the refrigeration system comprises:
- compressing a substance, comprising the target molecule, in a container; and
- conducting an airflow relative to the container.

16. A non-transitory computer readable medium storing instructions operable to cause one or more processors to perform operations comprising:
- determining a plurality of molecules from a database having elements restricted to one or more of carbon, hydrogen, oxygen, nitrogen, bromine, chlorine, fluorine, and sulfur;
- determining a sample of molecules from the plurality of molecules;
- training a machine learning model to predict one or more properties of a molecule, the one or more properties indicating susceptibility to a Barocaloric effect, the machine learning model trained based on the sample of molecules;
- applying the machine learning model to the plurality of molecules to predict the one or more properties for molecules of the plurality of molecules;
- determining a plurality of candidate molecules from the plurality of molecules, the plurality of candidate molecules determined based on the one or more properties predicted for molecules of the plurality of molecules; and determining a target molecule of the plurality of candidate molecules to implement in a refrigeration system, wherein the database includes at least $10^9$ molecules, the plurality of molecules includes at least $10^6$ molecules, and the plurality of candidate molecules includes at least $10^3$ molecules.

17. The non-transitory computer readable medium of claim 16, wherein determining the plurality of candidate molecules comprises:

determining molecules of the plurality of molecules having $T_{fusion}$ between 350K and 450K and $\Delta S_{fusion}$ less than a 30 J/(mol-K).

18. The non-transitory computer readable medium of claim 16, the operations further comprising:

ranking candidate molecules of the plurality of candidate molecules based on Euclidean distances between the one or more properties of the candidate molecules and one or more ideal values.

* * * * *